US012751989B2

(12) United States Patent
Magon

(10) Patent No.: US 12,751,989 B2
(45) Date of Patent: Oct. 6, 2026

(54) WATER SOLUBLE CURCUMINOIDS COMPOSITION FOR TREATING MOUTH AND THROAT CONDITIONS

(71) Applicant: Eran Magon, Tel Aviv (IL)

(72) Inventor: Eran Magon, Tel Aviv (IL)

( * ) Notice: Subject to any disclaimer, the term of this patent is extended or adjusted under 35 U.S.C. 154(b) by 726 days.

(21) Appl. No.: 18/011,706

(22) PCT Filed: Jun. 29, 2021

(86) PCT No.: PCT/IL2021/050801
§ 371 (c)(1),
(2) Date: Dec. 20, 2022

(87) PCT Pub. No.: WO2022/003685
PCT Pub. Date: Jan. 6, 2022

(65) Prior Publication Data

US 2023/0310536 A1 Oct. 5, 2023

Related U.S. Application Data

(60) Provisional application No. 63/045,214, filed on Jun. 29, 2020.

(51) Int. Cl.

| | |
|---|---|
| ***A61K 36/9066*** | (2006.01) |
| ***A61K 9/00*** | (2006.01) |
| ***A61K 36/484*** | (2006.01) |
| ***A61K 47/10*** | (2017.01) |
| ***A61P 1/02*** | (2006.01) |

(52) U.S. Cl.
CPC ........ *A61K 36/9066* (2013.01); *A61K 9/0056* (2013.01); *A61K 36/484* (2013.01); *A61K 47/10* (2013.01); *A61P 1/02* (2018.01)

(58) Field of Classification Search
CPC .............. A61K 36/9066; A61K 9/0056; A61K 36/484; A61K 47/10; A61K 8/35; A61K 9/0053; A61K 31/12; A61K 47/32; A61P 1/02; A61Q 11/00
See application file for complete search history.

(56) References Cited

U.S. PATENT DOCUMENTS

| | | | | |
|---|---|---|---|---|
| 5,861,415 | A | 1/1999 | Majeed et al. | |
| 8,759,562 | B2 | 6/2014 | Mei et al. | |
| 2005/0181036 | A1* | 8/2005 | Aggarwal | A61K 31/12 514/689 |
| 2007/0077315 | A1 | 4/2007 | Schoenborn | |
| 2008/0299220 | A1 | 12/2008 | Tamarkin et al. | |
| 2016/0256412 | A1 | 9/2016 | Majeed et al. | |

FOREIGN PATENT DOCUMENTS

| | | | |
|---|---|---|---|
| CN | 1961679 | A | 5/2007 |
| CN | 101554369 | A | 10/2009 |
| CN | 103142940 | A | 6/2013 |
| CN | 103920095 | A | 7/2014 |
| CN | 104147525 | A | 11/2014 |
| CN | 104996503 | A | 10/2015 |
| CN | 105194564 | A | 12/2015 |
| CN | 105999095 | A | 10/2016 |
| CN | 106075522 | A | 11/2016 |
| IN | 201741021536 | | 12/2018 |
| WO | 1996025939 | A1 | 8/1996 |
| WO | 2006022012 | A1 | 3/2006 |
| WO | 2007110871 | A2 | 10/2007 |
| WO | 2008051474 | A1 | 5/2008 |
| WO | 2010109482 | A2 | 9/2010 |
| WO | 2016140904 | A1 | 9/2016 |
| WO | 2017203359 | A1 | 11/2017 |
| WO | 2020087057 | A1 | 4/2020 |

OTHER PUBLICATIONS

Praditya D, Kirchhoff L, Bruning J, Rachmawati H, Steinmann J, Steinmann E. Anti-infective Properties of the Golden Spice Curcumin. Front Microbiol. May 3, 2019;10:912. doi: 10.3389/fmicb.2019.00912. PMID: 31130924; PMCID: PMC6509173. pp. 16.

* cited by examiner

*Primary Examiner* — Robert A Wax
*Assistant Examiner* — Quanglong N Truong
(74) *Attorney, Agent, or Firm* — The Roy Gross Law Firm, LLC; Roy D. Gross

(57) ABSTRACT

Composition for use in treating or ameliorating a mouth, tongue and/or throat medical condition comprising one or more curcuminoids and a hydrophilic carrier characterized having at least about 0.5% w/w curcuminoids out of the total weight of the composition being solvated by aqueous medium or the hydrophilic carrier.

17 Claims, No Drawings

WATER SOLUBLE CURCUMINOIDS COMPOSITION FOR TREATING MOUTH AND THROAT CONDITIONS

CROSS REFERENCE TO RELATED APPLICATIONS

This application is a National Phase of PCT Patent Application No. PCT/IL2021/050801 having International filing date of Jun. 29, 2021, which claims the benefit of priority of U.S. Provisional Patent Application No. 63/045,214, filed Jun. 29, 2020, the contents of which are all incorporated herein by reference in their entirety.

TECHNICAL FIELD

The invention relates to nutraceutical compositions. In particular, the invention relates to a composition that comprises curcuminoids. The invention also relates to compositions for treating mouth tongue and throat conditions.

BACKGROUND ART

There is a dramatic gap between the level mouth and throat disorders affect our quality of life and the available products for relief of pain that associated with these disorders. Mouth and throat disorders, such as canker sores, cold sores, leukoplakia, thrush and sore throat can make it hard to eat, drink, or even smile. Upper respiratory tract infection is one of the most common reasons for work/school absenteeism, and a causes enormous economy loss.

A sore throat is pain, scratchiness or irritation of the throat that often worsens when you swallow. The most common cause of a sore throat is pharyngitis. Acute throat infections are among the most common infectious diseases seen by family physician (1,2). They are responsible for 2% to 4% of all family physician visits. Viruses cause 85% to 95% of throat infections in adults and children younger than 5 years of age; for those aged 5 to 15 years, viruses cause about 70% of throat infections, with the other 30% due to bacterial infections.

Symptoms of a sore throat can vary depending on the cause. Signs and symptoms might include: Pain or a scratchy sensation in the throat, pain that worsens with swallowing or talking, difficulty swallowing, sore and swollen glands in throat or jaw, swollen and red tonsils, white patches or pus on your tonsils, hoarse or muffled voice Common infections causing a sore throat might result in other signs and symptoms, including: fever, cough, runny nose, sneezing, body aches, headache, nausea or vomiting.

Viruses that cause the common cold and flu (influenza) also cause most sore throats. Less often, bacterial infections cause sore throats.

Viral illnesses that cause a sore throat include: Common cold, Flu (influenza), Mononucleosis (mono), Measles, Chickenpox, Croup.

A number of bacterial infections can cause a sore throat. The most common is *Streptococcus pyogenes*, or group A streptococcus, which causes strep throat. Conventional medicine treatments of sore throat or other mouth and throat disorders are limited to administration of antibiotics and/or phenol in cases of a bacterial infection such as a streptococcus A infections, but are shorthand when the cause is non-bacterial. Mouth lesions that are associated with chemotherapy treatments are treated by administration of cortisone. To ameliorate the pain associated with these disorders, pain relief medicaments such as ibuprofen or acetaminophen are prescribed.

All of these treatments are associated with harmful side effects, especially in prolonged or repetitive use, and there is a high demand for natural alternatives. Natural products made of slippery elm, licorice root and marshmallow root are used for soothing pain related with mouth and throat sores. Inhaling vapors of turmeric boiled in water is another traditional method of treatment.

More than 3500 years ago, evidence has appeared in traditional Indian medicine about the effectiveness of turmeric, a spice derived from the perennial herb *Curcuma longa* L, as a medicinal plant for the treatment of various conditions including intestinal diseases, liver, skin and stones in the urinary tract.

The main active compounds in turmeric are three curcuminoids, namely curcumin (diferuloyl methane), demethoxy curcumin (p-hydroxycinnamoylferuloylmethane) and bis-demethoxy curcumin (p,p-dihydroxydicinnamoylmethane).

A recent review of the PubMed database has raised more than 10,000 scientific articles on turmeric and curcumin, the active ingredient of turmeric. However, curcumin, which shows positive results in most drug discovery assays (See for example Partoazar et al. Drug Res. 2016, 66, 660-665; Vaughn et al. *Phytother Res.* 2016 30:1243-64; Kia et al. J. Dent. 2015 12, 789-967; and Czekaj et al. *J. Physiol. Pharmacol.* 2016, 67, 261-75), is regarded as a false lead attracting undue experimental attention while failing to advance as viable therapeutic or drug leads. According to a 2017 review of more than 120 studies, curcumin has not been successful in any clinical trial, leading the authors to conclude that "curcumin is an unstable, reactive, non-bioavailable compound and, therefore, a highly improbable lead" (See Nelson et al. *J. Med. Chem.* 2017, 60, 1620-1637). Factors that limit the bioactivity of curcumin or its analogs include chemical instability, water insolubility, absence of potent and selective target activity, low bioavailability, limited tissue distribution, and extensive metabolism.

There is therefore a need to overcome the intrinsic shortcomings of curcumin in order be able utilize this promising compound for the benefit of patients suffering from various medical conditions. Compositions containing curcumin, demethoxy curcumin and bis-demethoxy curcumin, extracted from roots of turmeric and complexed with metal was disclosed in U.S. Pat. No. 5,861,415.

A preparative method and applications of a Zn(II)-curcumin complex and its solid dispersions were disclose in U.S. Pat. No. 8,759,562.

Povidone (polyvinylpyrrolidone, PVP) is used in the pharmaceutical industry as a synthetic polymer vehicle for dispersing and suspending drugs. It has multiple uses, including as a binder for tablets and capsules, a film former for ophthalmic solutions, to aid in flavoring liquids and chewable tablets, and as an adhesive for transdermal systems.

A curcuminoids composition comprising PVP and characterized 10%-15% w/w aqueous solubility of curcuminoids in water is disclosed in International Patent Application Publication No. WO 2016/140904.

SUMMARY OF INVENTION

Technical Problem

The object of the invention is to provide a composition, in particular a nutraceutical composition, for effectively treating and/or ameliorating a mouth tongue or throat disorder.

More specifically the object is to provide a composition, in particular a nutraceutical composition, for effectively treating and/or ameliorating a mouth tongue or throat disorder that comprises curcuminoids despite their bioavailability limitations, in particular due to their low solubility in aqueous solution and low absorption through the digestive system.

Solution To Problem

In a first aspect the invention provides a composition for treating or ameliorating at least one of a mouth, tongue and throat condition comprising curcuminoids and a hydrophilic carrier characterized by at least about 0.5% w/w curcuminoids out of the total weight of the composition being solvated by aqueous medium or being solvated by the hydrophilic carrier.

In some embodiments, the hydrophilic carrier is characterized by having a solubility rate of at least about 50 mg/ml of the hydrophilic carrier in water. The hydrophilic carrier may be characterized as a water hydrophilic carrier for the curcuminoids in an aqueous medium.

In some embodiments, the hydrophilic carrier is selected from lipid micelles, cyclodextrine and derivatives thereof, sugar alcohol, a water soluble polymer selected from phosphatyldicholine, polyethylene glycol methyl vinyl ether, polyethylene glycol, polyvinylpyrrolidone, polyvinyl alcohol, polyethyleneimine and poly[N-(2-hydroxypropyl)methacrylamide](PHPMA), and polyglutamic acid and copolymers thereof, cellulose and derivatives thereof, and mixtures thereof.

In some embodiments, the hydrophilic carrier is polyvinylpyrrolidone (PVP) optionally PVP K-30. In some embodiments, the composition comprises about 70 to about 80% w/w PVP K-30 out of the total weight of the composition.

In some embodiments, the composition is characterized by an aqueous solubility of the curcuminoids or by solubility of the curcuminoids in the hydrophilic carrier of at least about 0.5% w/w, about 1% w/w, or about 5% w/w out of the total weight of the composition.

In some embodiments, the composition is characterized by an aqueous solubility of curcuminoids of at least about 10% w/w out of the total weight of the composition.

In some embodiments, the composition comprises about 5 to about 15% w/w, in some embodiments about 10%, of curcuminoids out of the total weight of the composition.

In some embodiments, the curcuminoids are tetrahydrocurcuminoids.

In some embodiments, the curcuminoids are a mixture of curcumin, demothoxy curcumin and bis-demethoxy curcumin optionally complexed with metal, for example with zinc.

In some embodiments, the curcuminoids are in a form selected from at least one of curcumin-loaded solid lipid nanoparticles, nano-micelle curcumin, nano-particles of curcumin, and nano encapsulated curcumin.

In some embodiments, the curcuminoids are extracted from *Curcuma longa*, optionally from its rhizomes and optionally by ethyl acetate.

In some embodiments, the composition comprises a pharmaceutically acceptable carrier, excipient, flavoring agent such as Licorice extract, encapsulating agent, emulsifier or surfactant such as dioctyl sulfosuccinate, alkali salt such as sodium chloride or potassium chloride.

In some embodiments the composition comprises about 0.01 to about 5% w/w sodium chloride out of the total weight of the composition.

In some embodiments, the aqueous medium is selected from the group consisting of pure water, an aqueous emulsion, an aqueous suspension, an atomized aqueous solution, an aqueous elixir, and an aqueous syrup.

In some embodiments, the composition is in a form of an aerosol.

In some embodiments, the at least one of a mouth tongue and throat disorder is selected from at least one of aphthous stomatitis, gingivitis, gingvomatitis, periodontitis, transient lingual papilitis, tongue patches buccal ulcers such as sores of hand-foot- and mouth disease, oral thrush such as mouth fungal infection and Candida yeast infection of the mouth, pharyngitis, laryingitis, tonsillitis, leukoplakia, oral Lichen planus lesions, pemphigus vulgaris, black hairy tongue lesions, tongue patches, hoarseness.

In some embodiments, the treatment is prophylactic.

In some embodiments the composition is a pharmaceutical composition or a nutraceutical composition.

In another aspect the invention provides a method for treating and/or ameliorating a subject suffering from at least one of a mouth tongue and throat syndrome comprising administering an effective amount of a composition as defined above to a patient in need.

In some embodiments, the composition is administered to the patient in need at least once in every 2 to 6 hours.

In some embodiments, the composition is administered by spraying on the affected area 2 to 3 times every 2 to 3 hours.

About 200 mg of curcuminoids are administered to the patient in need every 2-3 hours.

In some embodiments, administering the composition to the patient in need is carried out by aerosol delivery to the sore throat.

In some embodiments the administering the composition to the patient in need is carried out by administering a chewing tablet comprising the composition (e.g. a gummy tablet such as a gummy bear), a dissolvable tablet such as a lozenge or a gelatinous patch comprising the composition, or a mouth wash solution comprising the composition.

In some embodiments the administering the composition is carried out by administering a capsule comprising the composition.

In some embodiments, the composition is administered to a patient in need at the affected area 1 to 3 times every 20 to 30 minutes during the first 2 to 4 hours and afterwards the composition is administered 1 to 3 times every 1 to 3 hours until relief in symptoms and optionally administered once daily for a week after relief in symptoms.

In some embodiments, the patient suffers from a disorder selected from at least one of pharyngitis, tonsillitis, laryngitis In a further aspect, the invention provides a method for prophylaxis of a mouth or throat condition comprising administering an effective amount of a composition as defined above to a patient in need optionally the composition is administered to the mouth tongue and/or the throat of the patient 1 to 3 times a day.

In yet another aspect the invention provides a use of a composition as defined above for treating or ameliorating, or for preparing a medicament for treating or ameliorating a buccal or pharynx disorder or for prophylactically treating a buccal or pharynx disorder.

In another aspect, the invention provides a process for preparing an aerosol for treating or prophylaxis of a mouth or throat disorder comprising the steps of:

obtaining a composition as defined above, dissolving the composition in water to obtain a curcumin-based aqueous solution, and packaging the solution in a spray bottle.

Advantageous Effects of Invention

The invention provides a nutraceutical composition that comprises water soluble curcuminoids that for the first time effectively treats mouth or throat disorders.

DESCRIPTION OF EMBODIMENTS

Although the invention is illustrated and described herein as embodied in an example composition, the invention is not limited to the details shown because various modifications and structural changes may be made without departing from the invention and the equivalents of the claims. However, the construction and method of operation of the invention together with additional objects and advantages thereof will be best understood from the following description of specific embodiments when read in connection with the accompanying examples.

The inventor of this invention has surprisingly found that using a composition comprising curcuminoids and a hydrophilic carrier characterized by having at least 5% w/w curcuminoids in an aqueous medium is effective for use in treating or ameliorating at least one of a mouth, tongue or throat condition. In some embodiments, the composition is for use in the treatment of a mouth tongue and throat condition. In some embodiments, the composition is for use in the amelioration of a mouth tongue and throat condition.

The term "condition" refers to medical conditions which may be a disease, a medical disorder, syndrome, pain, sore or lesion.

Therefore in a first aspect, the invention provides a composition for use in treating or ameliorating at least one of a mouth, tongue and throat condition comprising curcuminoids and a hydrophilic carrier characterized by at least 5% w/w curcuminoids in aqueous medium.

The term "treating" or any lingual variation thereof, as used herein, refers to the administering of a therapeutic amount of the composition described herein, which is effective to ameliorate undesired symptoms associated with a disease, to slow down the progression of the disease, slow down the deterioration of condition of the patient, to enhance the onset of remission period, slow down the irreversible damage caused in the progressive chronic stage of the disease, to delay the onset of said progressive stage, to lessen the severity or cure the disease, to affect a rapid recovery, or to prevent the disease from occurring or a combination of two or more of the above. The determination of the effectiveness of the composition can determined by testimonial of the patient or by objective monitoring of markers and indicators of the disease or symptoms, such as size of lesions, number of bacterial colonies, bacteria count, inflammation factor levels in blood count and so forth.

The term "prophylaxis" refers to prevent the manifestation of the disease onset or symptoms before they occur.

The term "mouth" refers to the entire buccal cavity including the buccal mucosa, the tonsi, the uvula, the gingiva (gum), the hard palate, the soft palate, the retromolar trigone, the floor of the mouth and the tongue. The term "throat" refers to the pharynx, larynx and vocal cords.

The composition of the invention is for use treating or ameliorating mouth, tongue and throat disorders and lesions in the broadest interpretation of the terms disorder and lesion. It is within the scope of the invention, that the composition is for use in treating or ameliorating inter alia any infection, swelling, and lesion that is a result of viral, fungal or bacterial infection, as a symptom of mal nutrition, acute or chronic autoimmune condition or as a result of a wound. The composition of the invention may also be used for prophylactic purposes, for example in order to prevent recurrence of pharyngitis (especially streptococcus B infections) or to prevent people at high risk of catching a contagious mouth or throat disease such as medical practitioners, teachers or family members of someone carrying a contagious mouth or throat disorder.

The effective amount for purposes herein may be determined by such considerations as known in the art. The effective amount is typically determined in appropriately designed clinical trials (dose range studies) and the person versed in the art will know how to properly conduct such trials in order to determine the effective amount. As generally known, the effective amount depends on a variety of factors including the distribution profile within the body, a variety of pharmacological parameters such as half-life in the relevant mucosal tissues, on undesired side effects, if any, on factors such as age and gender, and others.

The term curcuminoids refers to 1,7-diaryl-1,6-heptadiene-3,5-dione compounds. These include both tautomeric forms (keto and enol) of curcumin (diferuloyl methane also known as (E,E)-1,7-bis-(4-hydroxy-3-methoxyphenyl)-1,6-heptadiene-3,5,-dione), demthoxycurcumin, bis-demthoxycurcumin, the saturated derivative tetrahydrocurcumin. Within the scope of the invention, the term curcumin derivative means natural and synthetic curcumin derivatives. Synthetic derivatives of curcuminoids may be for example curcuminoids that are covalently linked to hydrophilic carriers (e.g. PEG, and derivatized PEG), and metal complexes of curcuminoids such as zinc complexes.

The composition may include curcuminoids that are extracted from the *Curcuma Longa* (Turmeric) plant. Methods for extracting curcuminoids from turmeric are known in the art. For example, the composition may include curcuminoids that are extracted by ethyl acetate from the rhizomes of *Curcuma longa*, but other methods of extraction may be employed. The extracted curcuminoids may be further recrystallized as known in the art.

When extracted from turmeric, the three main curcuminoids are curcumin, demthoxycurcumin and bis-demthoxycurcumin. The ratios between these three curcuminoids vary between the varieties, and may vary from season to season in the same variety. Curcumin is usually the main component in these extracts. In some embodiments, the composition of the invention includes a mixture of curcumin, demthoxycurcumin and bis-demthoxycurcumin. The composition may include a zinc complexed curcumin/zinc complexed demthoxycurcumin/zinc complexed bis-demthoxycurcumin mixture having a ratio of 1-99:1-99:1-99 w/w out of the total weight of curcuminoids. The composition may include a zinc complexed curcumin/zinc complexed demthoxycurcumin/zinc complexed bis-demthoxycurcumin mixture having a ratio of 10-80:1-50:1-50 w/w out of the total weight of curcuminoids. The composition may include a zinc complexed curcumin/zinc complexed demthoxycurcumin/zinc complexed bis-demthoxycurcumin mixture having a ratio of 30-70:10-40:10-40 w/w out of the total weight of curcuminoids. The composition of the invention may prepared from the commercially available water soluble curcuminoids compositions UC3 Clear™ from Sabinsa™ or AQUACUMIN from AVA Plant.

The curcuminoids may be in the form of curcumin-loaded solid lipid nanoparticles, nano-micelle curcumin, nano-particles of curcumin, and nano-encapsulated curcumin. The curcuminoids may be solvated as a solute in the aqueous medium (i.e. in water) and the may also be solvated in the hydrophilic carrier itself, i.e. the molecules of the hydrophilic carrier surround each curcuminoids molecule and isolate it from direct contact with water molecules. The term "solvated" means that curcuminoid molecules are surrounded by the molecules of the medium (i.e. water molecules) and/or molecules of the hydrophilic carrier. In some embodiments, not all of the curcuminoid content is solubilized, and a portion of the curcuminoids may be present for example as solid aggregates. The amount or concentration of solvated curcuminoids (the amount/concentration of the solute) may be determined by any commonly used applicable analytical method such as diffusion NMR.

The composition may contain a total of water solvated curcuminoids concentration of at least 0.5% w/w, 1% w/w, 5% w/w or 10% w/w out of the total weight of the aqueous solution. In some embodiments, the composition may contain a total of water solvated curcuminoids concentration of between 5% w/w to 15% w/w or between 10% w/w to 15% w/w out of the total weight of the aqueous solution. In some embodiments, the composition may contain a total concentration of curcuminoids that are solvated in the hydrophilic carrier of at least 0.5% w/w, 1% w/w, 5% w/w or 10% w/w out of the total weight of the composition. In some embodiments the composition may contain a total of curcuminoids concentration that are solvated in the hydrophilic carrier of between 5% w/w to 15% w/w or between 10% w/w to 15% w/w out of the total weight of the aqueous solution.

In some embodiments the composition may contain a total amount of curcuminoids of between 1% w/w to 20%, 5% w/w to 15% w/w or between 10% w/w to 15% w/w out of the total weight of the aqueous solution.

The term "total of curcuminoids concentration" means that the overall amount of the curcuminoids in the composition is calculated to determine the concentration, so each curcuminoid contributes a portion to the overall amount of curcuminoids. For Example, a composition weighing 100 mg may contain 6 mg curcumin, 5 mg demothoxycurcumin and 4 mg bisdemethoxycurcumin, so the total amount of curcuminoids is 15 mg and the total concentration of curcuminoids is 15 w/w % of the total weight of the composition. The solubility rate in water of each curcuminoid in said example may be 66.7%, so the total of water solvated curcuminoids concentration would be 10% w/w out of the total weight of the composition. In practice, the solubility rate may vary for each curcuminoids.

The composition includes a hydrophilic carrier that mitigates one of the major barriers for improving the bioavailability of the curcuminoids. The "hydrophilic carrier" means any substance or mixture of substances that may be used to enhance the solubility of the curcuminoids in the composition in an aqueous medium. The hydrophilic carriers used in this invention are characterized by having a solubility rate of at least about 50 mg/ml in water (i.e. 50 mg of the hydrophilic carrier in 1 ml water at 20° C.) in some embodiments—at least 80 mg/ml in water and in some embodiments at least 100 mg/ml in water.

The term "bioavailability," as used herein means the concentration of a curcuminoid in the blood (serum or plasma).

The hydrophilic carrier may be selected from lipid micelles (e.g. glycerides), cyclodextrine and derivatives thereof, sugar alcohol (e.g. xylitol, sorbitol and erythritol), glycerol, a water soluble polymer selected from phosphatyldicholine, polyethylene glycol methyl vinyl ether, polyethylene glycol, polyvinylpyrrolidone, polyvinyl alcohol, polyethyleneimine, poly[N-(2-hydroxypropyl)methacrylamide] (PHPMA), polyglutamic acid, polyoxyethylene sorbitan monolaurate, polyoxyethylene sorbitan monopalmitate, polyoxyethylene sorbitan monooleate, polyoxyeyhylene esters of saturated and unsaturated castor oil, and copolymers thereof, cellulose and derivatives thereof, ethoxylated monoglycerol esters, ethoxylated fatty acids and ethoxylated fatty acids of short and medium and long chain fatty acids and mixtures thereof. In some embodiments the hydrophilic carrier is a humectant. It is speculated that the humectant increases the permeability of an active agent through mucosal membrane.

In some embodiments the hydrophilic carrier is polyvinylpyrrolidone (PVP) also known as Povidone. The PVP may be used in a range of polymer grades e.g. K-12, K-15, K-25, K-30, and K-60.

The composition may contain an amount of hydrophilic carrier such that will obtain a total of water solvated curcuminoids concentration of at least 0.5% w/w, 1% w/w, 5% w/w or 10% w/w out of the total weight of the aqueous solution. In some embodiments the composition may contain an amount of hydrophilic carrier such that will obtain a total of water solvated curcuminoids concentration of between 5% w/w to 15% w/w or between 10% to 15% w/w out of the total weight of the aqueous solution. In some embodiments the composition may contain an amount of hydrophilic carrier such that the total concentration of curcuminoids that are solvated in the solubilizing agent are of at least 0.5% w/w, 1% w/w, 5% w/w or 10% w/w out of the total weight of the composition. In some embodiments the composition may contain an amount of hydrophilic carrier such that will obtain a total of curcuminoids concentration that are solvated in the solubilizing agent of between 5% w/w to 15% w/w or between 10% to 15% w/w out of the total weight of the aqueous solution. The required amount/concentration of hydrophilic carrier would thus vary depending on the hydrophilic carrier that is used and on the composition of curcuminoids that is solvated.

The person of skill in the art will know how to modify the amount of hydrophilic carrier in order to obtain this requirement. In some embodiments, the composition contains 50 to 90% w/w, 60 to 85% w/w, or 70 to 80% w/w of hydrophilic carrier, such as PVP K-30, out of the total weight of the composition.

The term "aqueous medium" should be construed to include for example pure water, an aqueous emulsion, an aqueous suspension, an atomized aqueous solution, an aqueous elixir, and an aqueous syrup. In most embodiments it is desirable that the only solvent used is water. However, in some embodiments other pharmaceutically or nutraceutically acceptable solvents may be used instead or together with water such as an alcohol, in particular ethanol in various ratios. Other possible solvents or co-solvents with water may be selected from propanol, isopropyl alcohol, glycol, acetic acid, propionic acid, phosphoric acid, fumaric acid, tartaric acid and it derivatives, lactic acid, maleic acid and malic acid. The composition may further include other active ingredients that are known to affect symptoms that are intra alio accompanied with mouth or throat disorders such as mucous-thinning or expectorant, anesthetics, other anti-inflamatory active ingredients, antiseptic agent, anti-bacterial agents or disinfectants agents.

In some embodiments, the composition may additionally include at least one additive, selected from antioxidants (e.g vitamin C, tocopherols butylated hydroxytoluene (BHT)), preservatives (e.g. beta hydroxy acid (BHA) such as salicylic acid, tert-butylhydroquinone (TBHQ), propylate and its derivatives, carboxylate salts (e.g. sodium benzoate and potassium sorbate) and mixtures thereof), nutraceuticals (e.g. licorice (*Glyderiza glabra*) extract, ginger and propolis extract), membrane-piercing agents, transmembrane penetrating enhancers (such as transcutol, isosorbide, oleic acid, propylene glycol, maltodextrines, cyclodextrines, etc.), and vitamins.

In some embodiments, the composition further includes an adjuvant that can increase the effect of the curcuminoids or increase their bioavailability or both. In some embodiments, the adjuvant is a botanical compound, i.e. a compound available from a plant. In some embodiments, the botanical compound is selected from at least one of a cannabinoid and piperine. In some embodiments, the adjuvant is piperine. Without being bound to theory, piperine may assist in increasing the bioavailability of curcuminoids. In some embodiments piperine is added to the composition in the form of pepper, in particular ground pepper.

The composition may be prepared as a pharmaceutical medicament or nutraceutical composition that may further comprise pharmaceutically or nutraceutically acceptable carriers including solvents, co-solvents, surfactants such as dioctyl sulfosuccinate, emulsifiers, vehicles, adjuvants, excipients, diluents, flavoring agent such as licorice extract, a sweetener (artificial or natural) such as glucose, fructose saccharine, dextrose and honey, flavor masking agents, solubilizers (hydrophilic carriers) such as detailed above, an encapsulating agent, an emulsifier and others as known in the art.

The term “pharmaceutical or nutraceutical acceptable carriers” refers to well-known compounds to those who are skilled in the art that are readily available and are chemically inert to the active compounds with no or little side effects or toxicity under the conditions of use.

The aqueous diluent may be selected from water, saline, dextrose solution, water/alcohol mixtures, aqueous solutions (such as sugar and sweetener solutions), or a buffer having a pH between 3 and 9 or any other isotonic solution or flavored water.

The composition can be prepared by common methods known in the art for preparing pharmaceutical or nutraceutical composition. For example the mixture can be prepared by dissolving a water soluble curcumin mixture in water using a mechanical stirrer or a magnetic stirrer in a preparative vessel. The mixing can take place in a broad range of temperatures, for example between 10 to 60° C. In some embodiments, the mixture is prepared at room temperature (i.e. between 20 to 25° C.).

In some embodiments the composition comprises 1-10% w/w licorice extract out of the total weight of the composition. In some embodiments, the composition comprises 3-8% w/w licorice extract out of the total weight of the composition. In some embodiments, the composition comprises 5-7% w/w licorice extract out of the total weight of the composition.

In some embodiments, the composition may comprise 0.01% w/w to 5% w/w, 0.1% to 3% w/w or 0.5% w/w to 2.5% w/w alkali salt. The alkali salt may be a lithium, sodium or potassium salt. The alkali salt may be an alkali halide salt. In some embodiment, the alkali salt is selected from lithium iodide, lithium chloride, sodium iodide, sodium chloride, potassium iodide or potassium iodide.

The composition of the invention may be formulated in any form that makes it feasible to bring the composition in contact with the affected area. In some embodiments, the composition is in the form of an aerosol. In other embodiments the composition is in the form of a lozenge. In yet other embodiments, the composition is in a form of a rapid dissolving edible film. All these form can be prepared by methods known to a person of skill in the art.

In some embodiments, the composition is an oral composition which can be formulated as granules, powder, capsules, tablet, film, emulsion, lozenge, a chewing gum, a chewable gum (e.g. gummy bears), a hard or soft gelatin capsule or a suspension. In some embodiments, the oral composition is enclosed in a soft gelatin capsule. In other embodiments, the composition is compressed into tablets. In some embodiments, the oral composition is formulated as a mouth wash by using one or more diluents in which the cannabinoid or a mixture thereof is dissolved, suspended or emulsified in the fluid carrier.

The mouth, tongue and throat disorders which the composition of the invention may be useful for treatment, amelioration or prophylaxis are selected from at least one of aphthous stomatitis, gingivitis, gingvomatitis, periodontitis, transient lingual papilitis, tongue patches, buccal ulcers, oral thrush (e.g. as a result of mouth fungal infection or Candida yeast infection of the mouth), pharyngitis, laryingitis, tonsillitis, leukoplakia, oral Lichen Planus lesions (including patches, plaques and ulcers), pemphigus Pemphigus Vulgaris, black hairy tongue lesions, tongue patches, hoarseness. The ulcers for which the composition is useful for may be symptomatic ulcers as a result of side effects of chemotherapy treatment, lack of vitamin B12, Iron, Folate and/or Zink, any autoimmune disease, an allergic response to any bacteria in the mouth, ulcers of hand-foot- and mouth disease, Helicobacter pylori, Herpes labialis (Herpes simplex infections) named also cold sores, Ulcerative Colitis, hormonal shift before or during menstruation, emotional stress, Irritable bowel syndrome, sensitivity to gluten, minor injury to the mouth from dental work, overzealous brushing, sports mishaps or an accidental cheek bite.

In some embodiments, the composition is for treating a disorder selected from at least one of pharyngitis, tonsillitis and laryngitis.

The invention further provides a method for treating and/or ameliorating a subject suffering from at least one of a mouth, tongue and throat syndrome comprising administering an effective amount of a composition as defined above to a patient in need.

In some embodiments, the effective amount is between 1 mg to 400 mg of curcuminoids per administered dose. In some embodiments, the effective amount is between 2 mg to 200 mg of curcuminoids per administered dose. In some embodiments, the effective amount is between 10 mg to 100 mg of curcuminoids per administered dose. In some embodiments, the effective amount is about 10 mg, 50 mg, 100 mg or 200 mg of curcuminoids per dose. All the amounts mentioned above relate to the amount of curcuminoids that are solvated in water.

The term “about” refers to a deviation of up to 10% of the given value it refers to. The term “between” in proximity to a first indicative number and a second indicative number or when the two indicative number describe a range, this is meant to include the first and second indicative numbers and all the fractional and integral numerals there between. It should be noted that where various embodiments are described by using a given range, the range is given as such merely for convenience and brevity and should not be construed as an inflexible limitation on the scope of the invention. Accordingly, the description of a range should be considered to have specifically disclosed all the possible sub-ranges as well as individual numerical values within that range.

In some embodiments, the composition is administered at least once every 1 to 12 hours, every 2 to 6 hours, or every 2 to 3 hours. In some embodiments the composition is administered once or twice every hour, every 2 to 12 hours, every 2 to 6 hours, or every 2 to 3 hours. In some embodiments, the composition is administered two or three times every 2 to 12 hours, every 2 to 6 hours, or every 2 to 3 hours.

In some embodiments, the composition is administered to a patient in need at the affected area 1 to 4 times every 10 to 60 minutes during the first 2 to 6 hours and afterwards the composition is administered 1 to 3 times every 1 to 6 hours until relief in symptoms and optionally administered once to three times daily for a 3 to 14 days after relief in symptoms In some embodiments, the composition is administered to a patient in need at the affected area 1 to 3 times every 20 to 30 minutes during the first 2 to 4 hours and afterwards the composition is administered 1 to 3 times every 1 to 3 hours until relief in symptoms and optionally administered once daily for a week after relief in symptoms.

In some embodiments, the composition is administered to a patient in need at the affected area once or twice every 20 to 30 minutes during the first 3 hours and afterwards the composition is administered once or twice every couple of hours until relief in symptoms and optionally administered once daily for a week after relief in symptoms.

In the embodiment wherein the method is for prophylaxis of a mouth or throat disorder then the composition is administered to the mouth tongue and/or the throat of the patient 1 to 3 times a day.

The invention also provides a use of the composition according to the invention for use in treating or ameliorating buccal or pharynx disorder or for prophylactically treating a buccal or pharynx disorder.

The invention further provides use of the composition according to the invention for preparation of a medicament for use in treating or ameliorating buccal or pharynx disorder or for prophylactically treating a buccal or pharynx disorder.

Administering the composition to the patient in need can be carried out by aerosol delivery (spraying) an aqueous solution comprising the composition to the sore throat or by taking a lozenge. In other embodiments, administering is of a rapid dissolving edible film.

In some embodiments the method is for treating a patient suffering from a disorder selected from at least one of pharyngitis, tonsillitis and laryngitis.

In some embodiments the method is for treating a patient suffering from a disorder selected from aphthous stomatitis, gingivitis, gingvomatitis, periodontitis, transient lingual papilitis, tongue patches, buccal ulcers, oral thrush (e.g. as a result of mouth fungal infection or Candida yeast infection of the mouth), pharyngitis, laryingitis, tonsillitis, leukoplakia, oral Lichen planus lesions (including patches, plaques and ulcers), pemphigus vulgaris, black hairy tongue lesions, tongue patches, hoarseness.

The ulcers for which the composition is useful for may be symptomatic ulcers as a result of side effects of chemotherapy treatment, lack of vitamin B12, Iron, Folate and/or Zink, any autoimmune disease, an allergic response to any bacteria in the mouth, ulcers of hand-foot- and mouth disease, Helicobacter pylori, Herpes labialis (Herpes simplex infections) named also cold sores, ulcerative colitis, hormonal shift before or during menstruation, emotional stress, Irritable bowel syndrome, sensitivity to gluten, minor injury to the mouth from dental work, overzealous brushing, sports mishaps or an accidental cheek bite.

EXAMPLE 1

8-10 gram of UC3 clear™ curcumin extract powder comprising 10-15% w/w curcuminoids purchased from Sabinsa™ were dissolved in a 1 L aqueous solvent.

(Composition A: 100% water, Composition B: 5.4:1.6:1 (v/v) water/glycerin/ethanol and Composition C: 2.8:1 (v/v) water/glycerol). Food grade reverse osmosis filtered water as used in the beverage industry was used. Ascorbic acid (0.5 gr) was added to mixtures of Composition B and C and potassium sorbate (2.0 gr) was also added to the mixture of composition C. Each solution was stirred at room temperature (ca. 20° C.) for 5 minutes while stirring with a magnetic stirrer. The solutions was distributed to separate 20 cc or 30 cc brown glass bottles with a pump with a long folding actuator purchased from Gil Plastic Products LTD Manufacturers of pharmaceutical packaging & plastic labware.

Nutraceutical compositions A-C each comprising 0.10-0.15% w/v curcuminoids in an aqueous solution ready for use as an aerosol were obtained. Each shot of solution (i.e. each application) contains about 13.3 microliter which contains about 130 to 195 microgram curcuminoids.

TABLE 1

Ingredients list of Composition A

| Ingredients | w/w % | 20.20 gr | E-number | Function |
|---|---|---|---|---|
| Water | 99.01 | 13.5 g | | solvent |
| CURCUMA LONGA EXTRACT | 0.99 | 0.2 g | | herb extract |

TABLE 2

Ingredients list of Composition B

| Ingredients | w/w % | 20.71 gr | E-number | Function |
|---|---|---|---|---|
| Water | 65.185 | 13.5 g | | solvent |
| glycerin | 24.142 | 5 g | E422 | Humectant |
| Alcohol 96% | 9.657 | 2 g | | solvent |
| CURCUMA LONGA EXTRACT | 0.965 | 0.2 g | | herb extract |
| ascorbic acid | 0.0516 | 0.01 | E300 | Antioxidant |

TABLE 3

Ingredients list of Composition C

| Ingredients | w/w % | 30 gr | E-number | Function |
|---|---|---|---|---|
| Water | 68.20 | 20.46 g | | solvent |
| glycerin | 30.58 | 9.174 g | E422 | Humectant |
| Potassium sorbate | 0.2 | 0.06 g | E202 | solvent |
| CURCUMA LONGA EXTRACT (uC3Clear) | 0.965 | 0.29 g | | herb extract |
| ascorbic acid | 0.0516 | 0.0155 | E300 | Antioxidant |

EXAMPLE 2

The water soluble curcuminoids aerosol of Composition A that was prepared according to Example 1 was administered to a patient suffering from a strep throat that was found to be Streptococcus A positive, by administering the aerosol to the affected area three times on each side of the throat directing the glands and three times at the center of the throat every couple of hours for 3 days. The patient began administration of antibiotics only after the relief of the symptoms.

The example shows that the composition of the invention is useful for treating and ameliorating sore throat due to inflammation of Streptococcus A.

EXAMPLE 3

The water soluble curcuminoids aerosol of Composition A that was prepared according to Example 1 was administered to a patient suffering from a viral sore throat (found to be Streptococcus A negative), by administering the aerosol to the affected area three times on each side of the throat directing the glands and three times at the center of the throat every couple of hours for 3 days.

The example shows that the composition of the invention is useful for treating and ameliorating viral sore throat.

EXAMPLE 4

The water soluble curcuminoids aerosol of Composition A, B or C that was prepared according to Example 1 is administered to a patient suffering from an aphthous stomatitis lesion three times every 2-3 hours directly on the lesion. The patient who generally suffers from such lesions for 7-10 days until healing, is expected to report full healing within three days This example can demonstrate that the composition of the invention is effective for treating and relieving symptoms of aphthous stomatitis.

EXAMPLE 5

The water soluble curcuminoids aerosol of Composition A, B or C that was prepared according to Example 1 is administered to a patient suffering from hand-foot- and mouth disease lesions three times every 2-3 hours. The patient who generally suffers from such lesions for 7-10 days until healing, is expected to report full healing within three days

The invention claimed is:

1. An aqueous composition for use in treating or ameliorating at least one of a mouth, tongue and throat condition, the composition comprising one or more curcuminoids, aqueous medium, and a hydrophilic carrier wherein at least about 0.5% w/w curcuminoids out of the total weight of the composition being solvated by the hydrophilic carrier, and wherein the composition is in a form of an aerosol.

2. The composition according to claim 1 wherein the hydrophilic carrier is characterized by at least one of: (i) having a solubility rate of at least about 50 mg/ml of hydrophilic carrier in water and (ii) being selected from cyclodextrine and derivatives thereof, sugar alcohol, a water soluble polymer selected from phosphatyldicholine, polyethylene glycol methyl vinyl ether, polyethylene glycol, polyvinylpyrrolidone, polyvinyl alcohol, polyethyleneimine and poly[N-(2-hydroxypropyl)methacrylamide](PHPMA), polyglutamic acid and copolymers thereof, cellulose and derivatives thereof, and mixtures thereof.

3. The composition according to claim 1 wherein at least one of:

(i) comprising 5 to 15% w/w curcuminoids out of the total weight of the composition;

(ii) comprising at least 10% w/w curcuminoids in an aqueous medium out of the total weight of the composition; or (iii) an aqueous solubility of the curcuminoids or by solubility of the curcuminoids in the hydrophilic carrier of at least 0.5% w/w, 1% w/w, or 5% w/w out of the total weight of the composition; holds true.

4. The composition according to claim 1, wherein the curcuminoids are selected from the group consisting of tetrahydrocurcuminoids, a mixture of curcumin, demethoxy curcumin and bis-demethoxy curcumin.

5. The composition according to claim 1, wherein the curcuminoids are characterized by at least one of: (i) being extracted from *Curcuma longa*; or (ii) being complexed with metal.

6. The composition according to claim 1, comprising 5-7% w/w licorice extract out of the total weight of the composition.

7. The composition according to claim 1, wherein the at least one of a mouth tongue, and throat disorder is selected from at least one of aphthous stomatitis, gingivitis, gingvomatitis, periodontitis, transient lingual papilitis, tongue patches, buccal ulcers, oral thrush selected from at least one of mouth fungal infection and *Candida* yeast infection of the mouth, pharyngitis, laryingitis, tonsillitis, leukoplakia, oral Lichen planus lesions, pemphigus vulgaris, black hairy tongue lesions, tongue patches, and hoarseness.

8. The composition according to claim 1, wherein the composition is a nutraceutical composition.

9. A method for treating and/or ameliorating a subject suffering from at least one of a mouth, tongue and throat syndrome comprising administering an effective amount of a composition as defined in claim 1 to a patient in need.

10. The method according to claim 9, wherein the composition is administered to the patient in need at least once in every 2 to 6 hours.

11. The method according to claim 9, wherein the composition is administered to the patient in need by spraying on the affected area 2 to 3 times every 2 to 3 hours.

12. The method according to claim 9, wherein about 200 mg of curcuminoids are administered every 2-3 hours.

13. The method according to claim 9, wherein administering the composition to the patient in need is carried out by aerosol delivery to a sore throat.

14. The method according to claim 9, wherein the composition is administered to a patient in need at the affected area 1 to 3 times every 20 to 30 minutes during the first 2 to 4 hours and afterwards the composition is administered 1 to 3 times every 1 to 3 hours until relief in symptoms and optionally administered once daily for a week after relief in symptoms.

15. The method according to claim 9, wherein the patient suffers from a disorder selected from at least one of pharyngitis, tonsillitis, and laryngitis.

16. A method for prophylaxis of a mouth or throat disorder comprising administering an effective amount of a composition as defined in claim 1 to a patient in need.

17. The method according to claim 16, wherein the composition is administered to the mouth, tongue and/or the throat of the patient 1 to 3 times a day.

* * * * *